(12) United States Patent
Barrandon et al.

(10) Patent No.: US 8,420,761 B2
(45) Date of Patent: Apr. 16, 2013

(54) COMPOUNDS HAVING A GUANIDINE STRUCTURE AND USE OF SAME AS ORGANOPOLYSILOXANE POLYCONDENSATION CATALYSTS

(75) Inventors: Georges Barrandon, Mornant (FR); Delphine Blanc, Lyons (FR); Christian Maliverney, Saint Julien sur Bibost (FR); Hervé Parisot, Lentilly (FR)

(73) Assignee: Bluestar Silicones France, Cedex (FR)

( * ) Notice: Subject to any disclaimer, the term of this patent is extended or adjusted under 35 U.S.C. 154(b) by 61 days.

(21) Appl. No.: 12/934,496

(22) PCT Filed: Mar. 24, 2009

(86) PCT No.: PCT/EP2009/053425
§ 371 (c)(1),
(2), (4) Date: Dec. 16, 2010

(87) PCT Pub. No.: WO2009/118307
PCT Pub. Date: Oct. 1, 2009

(65) Prior Publication Data
US 2011/0098392 A1 Apr. 28, 2011

(30) Foreign Application Priority Data
Mar. 28, 2008 (FR) ...................................... 08 01707

(51) Int. Cl.
C08G 77/08 (2006.01)
C07C 277/00 (2006.01)

(52) U.S. Cl.
USPC ............... 528/21; 524/268; 524/588; 528/34; 564/230

(58) Field of Classification Search .......................... None
See application file for complete search history.

(56) References Cited

U.S. PATENT DOCUMENTS

| | | | |
|---|---|---|---|
| 4,515,932 A | 5/1985 | Chung | |
| 4,528,353 A | 7/1985 | Lucas et al. | |
| 4,563,498 A | 1/1986 | Lucas | |
| 5,371,164 A * | 12/1994 | Kobayashi et al. | 528/18 |
| 5,519,104 A | 5/1996 | Lucas | |
| 2005/0014894 A1 | 1/2005 | Flannigan et al. | |
| 2009/0182091 A1* | 7/2009 | Noro et al. | 524/588 |

FOREIGN PATENT DOCUMENTS

| | | |
|---|---|---|
| EP | 0885933 | 12/1998 |
| EP | 1985666 | 10/2008 |
| FR | 2557582 | 7/1985 |
| FR | 2786497 | 6/2000 |
| JP | 2005-105235 A * | 4/2005 |
| WO | 2004/020525 | 3/2004 |
| WO | 2007/094276 | 8/2007 |
| WO | WO 2007/094272 * | 8/2007 |

OTHER PUBLICATIONS

Machine-generated translation of JP 2005-105235 into English.*
"Catalytic Addition of Amine N-H Bonds to Carbodiimides by Half-Sandwich Rare Earth Metal Complexes: Effcient Synthesis of Substituted Guanidines through Amibne Protonolysis of Rare-Earth Metal Guanidates" authored by Zhang et al. and published in Chem. Eur. J. (2007) 13, 4037-4051.*
International Search Report of PCT/EP2009/053425, dated Oct. 2, 2009 (6 pages).
Katritzky et al., "The Preparation of 1,2,3-Trisubstituted Guanidines," 2005, pp. 1664-1675.

* cited by examiner

*Primary Examiner* — Marc Zimmer
(74) *Attorney, Agent, or Firm* — Baker Donelson Bearman Caldwell & Berkowitz, PC

(57) ABSTRACT

The present invention relates to an organopolysiloxane composition that can be vulcanized at room temperature into an elastomer that is crosslinked by polycondensation and that does not contain alkyltin-based catalysts which exhibit toxicity problems. The invention also relates to novel polycondensation catalysts having a guanidine structure, in silicone chemistry, and to the uses thereof as catalysts for the organopolysiloxane polycondensation reaction.

17 Claims, 1 Drawing Sheet

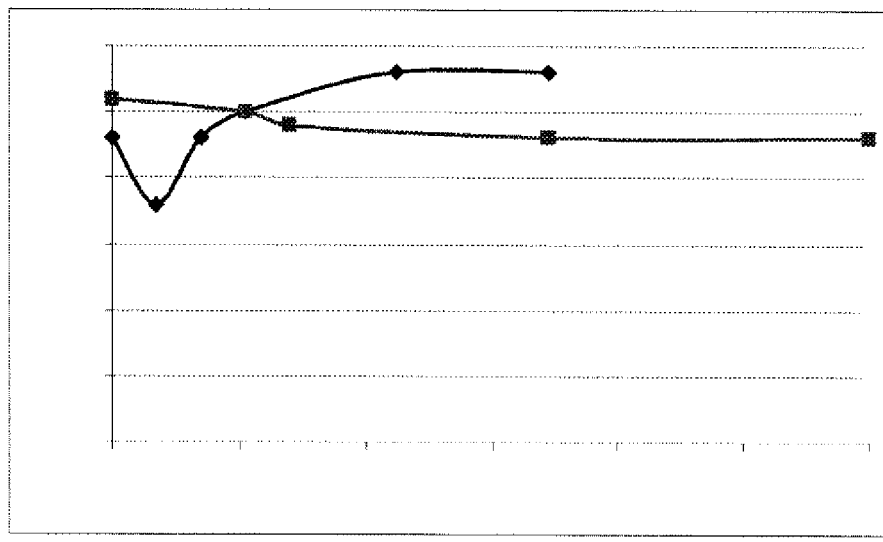
Properties after heat treatment at 220°C

COMPOUNDS HAVING A GUANIDINE STRUCTURE AND USE OF SAME AS ORGANOPOLYSILOXANE POLYCONDENSATION CATALYSTS

CROSS REFERENCE TO RELATED APPLICATIONS

This application is a §371 National Stage Application of PCT/EP2009/053425 filed Mar. 24, 2009, which claims priority to French Application 08 01707 filed Mar. 28, 2008.

BACKGROUND

1. Field of the Invention

The present invention relates to an organopolysiloxane composition that can be vulcanized at room temperature into an elastomer that is crosslinked by polycondensation and that does not contain alkyltin-based catalysts which exhibit toxicity problems.

The invention also relates to novel polycondensation catalysts having a guanidine structure, in silicone chemistry, and to the uses thereof as catalysts for the organopolysiloxane polycondensation reaction.

2. Description of Related Art

Formulations of elastomers that crosslink via polycondensation generally involve a silicone oil, generally a polydimethylsiloxane, with hydroxyl end groups, optionally prefunctionalized with a silane so as to have alkoxy ends, a crosslinking agent, a polycondensation catalyst, conventionally a tin salt or an alkyl titanate, a reinforcing filler and other optional additives such as bulking fillers, adhesion promoters, colorants, biocidal agents, etc.

These room-temperature vulcanizing organopolysiloxane compositions are well known and are classified into two different groups: single-component (RTV-1) compositions and two-component (RTV-2) compositions.

The term "RTV" is the acronym for "Room Temperature Vulcanizing".

During crosslinking, water (either provided by atmospheric moisture in the case of RTV-1 compositions, or introduced into a part of the composition in the case of RTV-2 compositions) enables the polycondensation reaction, which results in the formation of the elastomeric network.

Generally, single-component (RTV-1) compositions crosslink when they are exposed to moisture from the air, i.e. they cannot crosslink in an enclosed medium. For example, the single-component silicone compositions used as sealants or adhesives cold-crosslink according to a mechanism of hydrolysis of reactive functions of the acetoxysilane, ketiminoxysilane, alkoxysilane, etc., type, followed by condensation reactions between silanol groups formed and other residual reactive functions. The hydrolysis is generally carried out by virtue of water vapor which diffuses into the material from the surface exposed to the atmosphere. Generally, the kinetics of the polycondensation reactions is extremely slow; these reactions are therefore catalyzed by a suitable catalyst. As catalysts which are employed, use is most often made of catalysts based on tin, titanium or an amine or compositions of these catalysts. Catalysts based on tin (cf. in particular FR-A-2 557 582) and on titanium (cf. in particular FR-A-2 786 497) are catalysts that are very effective. Single-component silicone elastomers with —Si(OR) ends are sometimes referred to as alkoxy elastomers.

As regards two-component compositions, they are sold and stored in the form of two-components, a first component containing the base polymer materials and the second component containing the catalyst. The two components are mixed at the time of use and the mixture crosslinks in the form of a relatively hard elastomer. These two-component compositions are well known and are described, in particular, in the book by Walter Noll "Chemistry and Technology of Silicones" 1968, $2^{nd}$ edition, on pages 395 to 398. These compositions essentially comprise four different ingredients:

an α,ω-dihydroxydiorganopolysiloxane reactive polymer, a crosslinking agent, generally a silicate or a polysilicate, a tin catalyst, and
water.

Usually, the condensation catalyst is based on an organic tin compound. Indeed, many tin-based catalysts have already been proposed as crosslinking catalysts for these RTV-1 or RTV-2 compositions. Conventional polycondensation catalysts comprise dialkyltin compounds, in particular dialkyltin dicarboxylates such as dibutyltin dilaurate and dibutyltin diacetate, alkyl titanate compounds such as tetrabutyltitanate or tetraisopropyltitante, and titanium chelates (EP-A-0 885 933, U.S. Pat. No. 5,519,104, U.S. Pat. No. 4,515,932, U.S. Pat. No. 4,563,498, U.S. Pat. No. 4,528,353).

However, the alkyltin-based catalysts, although very effective, usually colorless, liquid and soluble in silicone oils, have the drawback of being toxic (CMR2 toxic for reproduction).

Thus, international application WO 2004/020525 describes single-component (RTV-1) silicone compositions used as sealants or adhesives and which cold-crosslink when they are exposed to the moisture in the air and which comprise, in addition to the usual components:

a specific and essential crosslinking agent (D) which is a silane comprising 1-methylvinyloxy functions, known for its strong reactivity compared with that of the conventional crosslinking agents, and catalysts which are organic derivatives comprising imine functions, of formula (I) or (II) below:

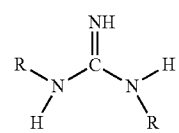

(I)

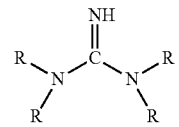

(II)

with R being a specific radical chosen from the following groups: methyl, isopropyl, phenyl and ortho-tolyl. Examples of these organic derivatives of imine type are 1,3-diphenylguanidine, 1,3-di-o-tolyl-guanidine, 1,3-dimethylguanidine and 1,1,3,3-tetra-methylguanidine, which is the preferred derivative. These derivatives have the particularity of possessing an unsubstituted imine function, i.e. a function of the C=NH type.

It should be noted that a conventional crosslinking agent of trialkoxysilane type, component (E), is still used in combination with the crosslinking agent (D) which is a silane known for its strong reactivity due to the presence of functions of 1-methylvinyloxy type.

However, the problem associated with the use of the organic catalysts comprising imine functions described in international application WO 2004/020525 is that they must be used in the presence of specific crosslinking agents that are very reactive and expensive (silanes comprising 1-methylvinyloxy functions), that is to say that conventional crosslinking agents having simple structures, which are very widely used in RTV-1 or RTV-2 formulations, for instance alkyltrialkoxysilanes, alkyl silicates or poly(alkyl silicate)s, cannot be combined with them without the obligatory presence of a very reactive crosslinking agent such as the silane with 1-methyl-vinyloxy functions. This is because, without the presence of this very reactive silane, the crosslinking of the composition into an elastomer is then insufficient and does not make it possible to obtain good mechanical properties. Thus, the 1,1,3,3-tetramethylguanidine derivative, which is presented in the preferred embodiment of this patent application, when it is used with a conventional crosslinking agent, for instance a poly(alkyl silicate), and without the presence of a reactive silane comprising methylvinyloxy functions, in a single-component RTV (RTV-1), the crosslinking of the system is then insufficient and cannot generate a silicone elastomer.

These problems with reactivity of the crosslinking agent, for example, in single-component (RTV-1) silicone compositions are well known by those skilled in the art. Indeed, the alkoxysilane crosslinking agents most widely used are those which have methoxy groups for their intrinsic reactivities. However, one of the problems associated with the use of alkoxysilanes of this type is that methanol is given off and is a source of problems in terms of health and safety.

For a sustainable development, it therefore appears to be necessary to develop other, nontoxic, catalysts for the organopolysiloxane polycondensation reaction which can be used in the crosslinking of both single-component elastomer compositions and two-component elastomer compositions. In addition, these catalysts should be usable irrespective of the type of crosslinking agent used.

Another important aspect for an organopolysiloxane polycondensation reaction catalyst is the working time (pot-life), i.e. the time during which the composition can be used after mixing, without it curing. This time should be sufficiently long to allow its use, but sufficiently short to obtain a handleable molded object at the latest a few minutes or a few hours after it has been produced. The catalyst should therefore make it possible to obtain a good compromise between the time during which the catalyzed mixture can be used and the time after which the molded object is handleable (these times depend on the intended application, for instance the molding or the production of seals). In addition, the catalyst should confer, on the catalyzed mixture, a spreading time which does not vary according to the storage time.

SUMMARY

It also appears to be necessary to provide a two-component (RTV-2) organopolysiloxane composition which has, at the same time, the following properties:
1) a rapid setting speed at ambient temperature (surface and enclosed) while at the same time maintaining a pot-life that is sufficiently long (of the order of a few minutes) to allow its use,
2) good mechanical properties after crosslinking,
3) good extrudability, and
4) good resistance to "reversion" of the elastomer derived from the crosslinking of the composition. This is because, when these elastomers are subjected to heating immediately or slightly after crosslinking thereof, a phenomenon that specialists refer to as "reversion" very often occurs. During this heating, the elastomers liquefy, in particular core-liquefy. This "reversion" can already occur at temperatures above 80° C. However, in most cases, it occurs at temperatures above 100° C., and it is particularly marked when the elastomers are heated in the total or almost total absence of air, i.e. when, during the heating, the elastomers are in a completely enclosed system. This reversion first results, in a first phase, in a loss of Shore A hardness, and then, when the heat treatment is maintained, it is followed by a second phase where an increase in the Shore A hardness is again observed owing to residual crosslinking of the fragments generated during the first phase. This "reversion" therefore constitutes a very troublesome drawback, in particular for certain applications where the cured elastomers are heated after crosslinking or are subjected to thermal stresses shortly after their crosslinking, by virtue of the intended application.

Thus, one of the essential objectives of the present invention is to propose a catalyst which is nontoxic but which continues to satisfy at the same time the constraints of storage, of use and of crosslinking of the two types of single-component and two-component elastomer compositions while at the same time being usable irrespective of the type of crosslinking agent used.

Another essential objective of the present invention is therefore to propose a novel nontoxic catalyst which allows, with the moisture in the air, both surface crosslinking but also core crosslinking which is as complete as possible.

Another essential objective of the present invention is to provide a single-component (RTV-1) and two-component (RTV-2) organopolysiloxane composition comprising a catalyst according to the invention and satisfying the criteria stated above, and in particular making it possible to prepare elastomers having good reversion resistance.

These objectives, among others, are achieved by the present invention which relates, first of all, to an organopolysiloxane composition which does not contain any metal catalyst and which is characterized in that it comprises, firstly, a silicone base B comprising at least one polyorganosiloxane oil which can be crosslinked via a polycondensation reaction so as to form a silicone elastomer and, secondly, a catalytically effective amount of at least one polycondensation catalyst A which is a nonsilylated organic compound corresponding to general formula (I):

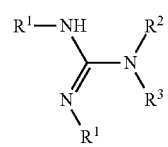
(I)

in which:
the $R^1$ radicals, which may be identical or different, represent, independently of one another, a linear or branched monovalent alkyl group, a cycloalkyl group, a (cycloalkyl)alkyl group, the ring being substituted or unsubstituted and being able to comprise at least one heteroatom, or a fluoroalkyl group,
the $R^2$ radical represents a hydrogen atom, a linear or branched monovalent alkyl group, a cycloalkyl group, an alkyl group substituted with a ring, which is substituted or unsubstituted and which can comprise at least one heteroatom, an aromatic group, an arylalkyl group, a fluoroalkyl group, an alkylamine group or an alkylguanidine group, and
the $R^3$ radical represents a linear or branched monovalent alkyl group, a cycloalkyl group, an alkyl group substituted with a ring, which is substituted or unsubstituted and which can comprise at least one heteroatom, an arylalkyl group, a fluoroalkyl group, an alkylamine group or an alkylguanidine group, when the R² radical is not a hydrogen atom, the R² and R³ radicals can be linked so as to form a 3-, 4-, 5-, 6- or 7-membered aliphatic ring optionally substituted with one or more substituents, and with the additional condition that the R¹, R² and R³ radicals do not comprise a silicon atom.

DETAILED DESCRIPTION OF A PREFERRED EMBODIMENT

To achieve this objective, the applicant has, to its credit, demonstrated, entirely surprisingly and unexpectedly, that the nonsilylated compounds corresponding to general formula (I) make it possible to catalyze the organopolysiloxane polycondensation reaction and can be used in the crosslinking of both single-component and two-component elastomer compositions, irrespective of the type of crosslinking agent used.

It is also to the inventors' credit to have overcome the technical prejudice, as taught, for example, by international application WO 2004/020525, which claimed that, up until now, structurally close catalysts, such as 1,3-diphenylguanidine, 1,3-di-o-tolylguanidine, 1,3-dimethylguanidine or 1,1,3,3-tetramethylguanidine, had to be combined with very reactive and expensive specific crosslinking agents (silanes comprising 1-methylvinyloxy functions) in order to crosslink formulations of RTV type.

The nonsilylated compounds according to the invention corresponding to general formula (I) are 1,2,3-tri-substituted and 1,2,3,3-tetrasubstituted guanidines and have the advantage of being liquid, colorless, odorless and soluble in silicone matrices. The nonsilylated guanidines according to the invention are used in the silicone systems to be crosslinked at very low contents, and make it possible, according to the content, to adjust the pot-life to the application while at the same time guaranteeing that the elastomers obtained have an excellent hardness, and also an excellent thermal stability, thus eliminating the problems associated with the reversion phenomena.

According to one preferred embodiment, the poly-condensation catalyst A is a nonsilylated organic compound corresponding to general formula (I) and in which:
the R₁ radicals, which may be identical or different, and the R₃ radical are chosen, independently of one another, from the group consisting of: an iso-propyl radical, a cyclohexyl radical and a linear or branched, monovalent $C_1$-$C_{12}$ alkyl radical,
the R₂ radical represents a hydrogen atom, a linear or branched monovalent alkyl group, a cycloalkyl group, an alkyl group substituted with a ring, which is substituted or unsubstituted and which can comprise at least one heteroatom, an arylalkyl group, a fluoroalkyl group, an alkylamine group or an alkylguanidine group, and
when the R² radical is not a hydrogen atom, the R² and R³ radicals can be linked so as to form a 3-, 4-, 5-, 6- or 7-membered aliphatic ring optionally substituted with one or more substituents.

Polycondensation catalysts A which are particularly preferred are nonsilylated organic compounds chosen from the group consisting of the following compounds (A1) to (A6):

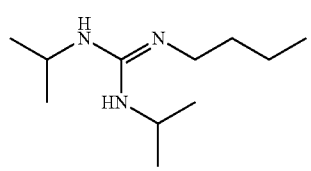
(A1)

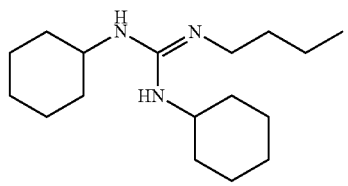
(A2)

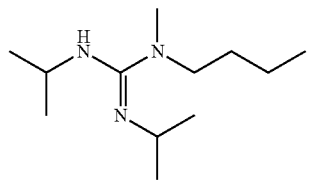
(A3)

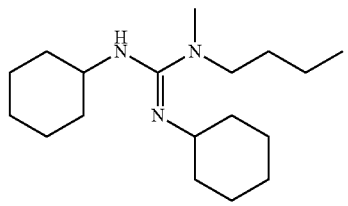
(A4)

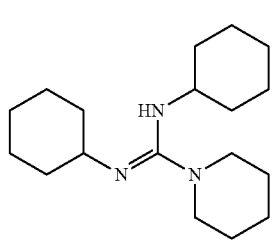
(A5)

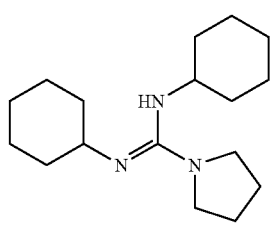
(A6)

The amount of polycondensation catalysts A according to the invention is between 0.1% and 10% by weight of the total mass, preferably between 0.1% and 50, whether it is a single-component or two-component preparation.

According to another preferred embodiment, the composition according to the invention as described above is characterized in that it also comprises a catalytically effective amount of at least one poly-condensation catalyst A as defined above and a silicone base B comprising:
at least one polyorganosiloxane oil C capable of crosslinking by polycondensation to give an elastomer;
optionally, at least one crosslinking agent D;
optionally, at least one adhesion promoter E; and
optionally, at least one siliceous, organic and/or nonsiliceous mineral filler F.

For the implementation of the invention, the silicone base B can comprise:
for 100 parts by weight of at least one poly-organosiloxane oil C capable of crosslinking by polycondensation, which is an α,ω-dihydroxydiorganopolysiloxane reactive polymer of which the organic radicals are hydrocarbon-based radicals, preferably chosen from the group consisting of: alkyls containing from 1 to 20 carbon atoms; cycloalkyls containing from 3 to 8 carbon atoms;

alkenyls containing from 2 to 8 carbon atoms and cycloalkenyls containing from 5 to 8 carbon atoms, from 0.1 to 60 parts by weight of at least one crosslinking agent D chosen from the group constituted of: polyalkoxysilanes, products originating from the partial hydrolysis of a polyalkoxysilane, and polyalkoxysiloxanes, from 0 to 60 parts by weight of an adhesion promoter E as described above, from 0 to 250 parts by weight, preferably from 5 to 200 parts by weight, of at least one siliceous, organic and/or nonsiliceous mineral filler F, from 0.001 to 10 parts by weight of water, from 0 to 100 parts by weight of at least one non-reactive, linear polyorganosiloxane polymer G consisting of a linear homopolymer or copolymer of which, per molecule, the monovalent organic substituents, which may be identical to or different from one another, and which are bonded to the silicon atoms, are chosen from alkyl, cycloalkyl, alkenyl, aryl, alkylarylene and arylalkylene radicals, from 0 to 20 parts by weight of a coloring base or of a coloring agent H, from 0 to 70 parts by weight of polyorganosiloxane resins I, and from 0 to 20 parts of auxiliary additives J known to those skilled in the art, such as plasticizers, crosslinking retardants, mineral oils, anti-microbial agents or heat stabilizers, such as titanium, iron or cerium oxides.

From 0.1 to 50 parts by weight of at least one poly-condensation catalyst A according to the invention and as described above are added to said silicone base B.

The invention also relates to a two-component system which is a precursor of the organopolysiloxane composition according to the invention and as described above, said composition being vulcanizable to give a silicone elastomer via polycondensation reactions and being characterized in that it is in two separate parts P1 and P2 intended to be mixed so as to form said composition, and in that one of these parts comprises the polycondensation catalyst A according to the invention and as defined above as catalyst of the reaction for polycondensation of organopolysiloxanes and the crosslinking agent D, whereas the other part is free of the abovementioned species and comprises:

for 100 parts by weight of the polyorganosiloxane oil(s) C capable of crosslinking by polycondensation to give an elastomer, and from 0.001 to 10 part(s) by weight of water.

Another subject of the invention consists of a single-component polyorganosiloxane composition which is stable during storage in the absence of moisture and which crosslinks, in the presence of water, to give an elastomer, characterized in that it comprises:

at least one crosslinkable linear polyorganosiloxane oil C which has functionalized ends of alkoxy, oxime, acyl and/or enoxy type, preferably alkoxy type, at least one crosslinking agent D, at least one filler F, and at least one catalyst for the polycondensation reaction which is the polycondensation catalyst A according to the invention and as defined above.

According to one preferred embodiment, the single-component polyorganosiloxane composition described above is characterized in that the crosslinkable linear polyorganosiloxane oil C having functionalized ends of alkoxy type is prepared in situ by reacting, in the presence of a catalytically effective amount of lithium hydroxide, a linear diorganopolysiloxane, comprising a hydroxyl group bonded to a silicon atom at each chain end, with at least one polyalkoxysilane of formula (II) below:

$$(R^4)_c(R^5)_a Si(OR^6)_{4-(a+c)} \quad (II)$$

in which:

a is equal to 0, 1 or 2, c is equal to 0, 1 or 2, the sum a+c is equal to 0, 1 or 2, $R^4$ represents an aliphatic, cyclanic or aromatic, substituted or unsubstituted, and saturated or unsaturated $C_1$ to $C_{13}$ hydrocarbon-based monovalent radical, it being possible for $R^4$ to be identical to $R^5$, $R^5$ represents an aliphatic, cyclanic or aromatic, substituted or unsubstituted, and saturated or unsaturated $C_1$ to $C_{13}$ hydrocarbon-based monovalent radical which can comprise an epoxy, primary, secondary or tertiary amine, or mercapto function, and $R^6$ represents an aliphatic organic radical containing from 1 to 8 carbon atoms, chosen in particular from alkyl radicals, alkyl ether radicals, alkyl ester radicals, alkyl ketone radicals, alkylcyano radicals and aralkyl radicals containing from 7 to 13 carbon atoms, it being understood that the alkoxy groups of the silane of formula (II) can each have a different meaning for $R^6$ or the same meaning.

According to one preferred embodiment, it is advantageous for the crosslinking agent D or the poly-alkoxysilane of formula (II) to be chosen from the group consisting of:

vinyltriethoxysilane, methyltriethoxysilane, propyltriethoxysilane, 1,2-bis(triethoxysilyl)ethane, $C_2H_5Si(OC_2H_5)_3$, and $Si(OC_2H_5)_4$.

This is because, with this type of crosslinking agent, there is no longer any release of methanol, as with the conventional trimethoxysilane crosslinking agent, thus solving many health and safety problems.

According to another of the aspects of the present invention, the subject thereof is also an elastomer obtained by crosslinking and curing of the two-component system according to the invention as defined above, of the single-component polyorganosiloxane composition according to the invention as defined above or of the composition according to the invention as defined above.

Another subject of the invention consists of novel compounds of formulae:

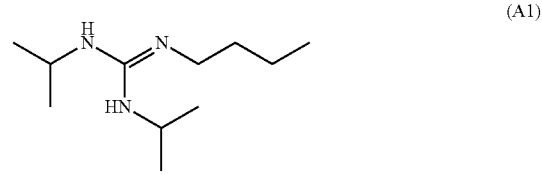

(A1)

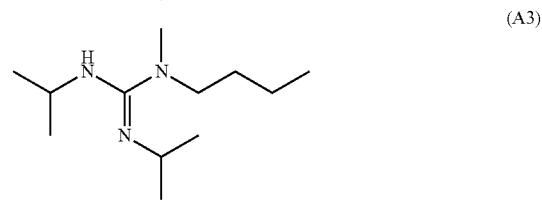

(A3)

(A4)

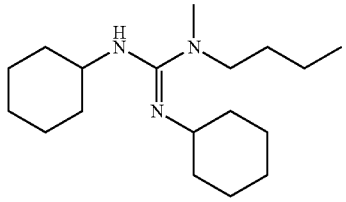

Another subject of the invention consists of the use, for catalyzing the organopolysiloxane polycondensation reaction, of a polycondensation catalyst A which is a nonsilylated organic compound corresponding to general formula (I):

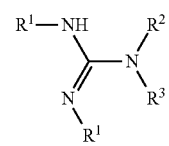
(I)

in which:

- the $R^1$ radicals, which may be identical or different, represent, independently of one another, a linear or branched monovalent alkyl group, a cycloalkyl group, a (cycloalkyl)alkyl group, the ring being substituted or unsubstituted and being able to comprise at least one heteroatom, or a fluoroalkyl group,
- the $R^2$ radical represents a hydrogen atom, a linear or branched monovalent alkyl group, a cycloalkyl group, an alkyl group substituted with a ring, which is substituted or unsubstituted and which can comprise at least one heteroatom, an aromatic group, an arylalkyl group, a fluoroalkyl group, an alkylamine group or an alkylguanidine group, and
- the $R^3$ radical represents a linear or branched monovalent alkyl group, a cycloalkyl group, an alkyl group substituted with a ring, which is substituted or unsubstituted and which can comprise at least one heteroatom, an arylalkyl group, a fluoroalkyl group, an alkylamine group or an alkylguanidine group,
- when the $R^2$ radical is not a hydrogen atom, the $R^2$ and $R^3$ radicals can be linked so as to form a 3-, 4-, 5-, 6- or 7-membered aliphatic ring optionally substituted with one or more substituents, and
- with the additional proviso that the $R^1$, $R^2$ and $R^3$ radicals do not comprise a silicon atom.

According to one preferred embodiment, the use according to the invention for catalyzing the organopolysiloxane polycondensation reaction is carried out using a polycondensation catalyst A which is a non-silylated organic compound chosen from the group consisting of the following compounds (A1) to (A6):

(A1)

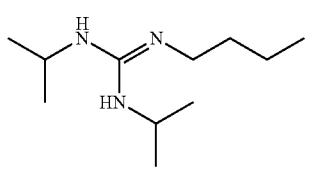

(A2)

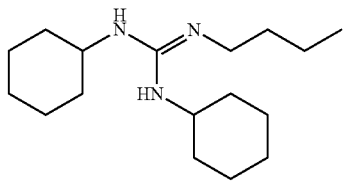

(A3)

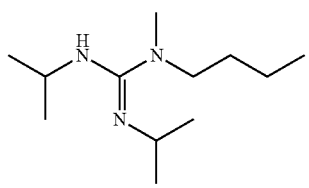

(A4)

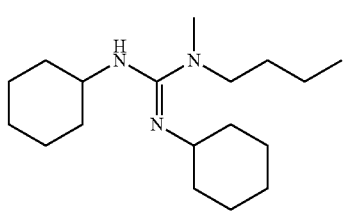

(A5)

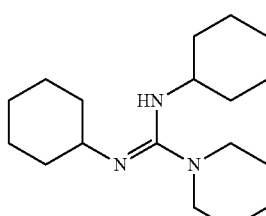

(A6)

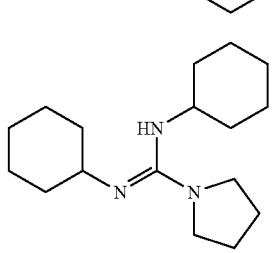

The catalysts in accordance with the present invention are nontoxic, unlike the alkyltin-based catalysts. Furthermore, they make it possible to achieve, both in single-component and two-component compositions, silicone polycondensation rates that are as high or even better than those obtained with these alkyltin-based catalysts.

Description of the Silicone Base B:

The silicone bases used in the present invention that crosslink and cure via polycondensation reactions are well known. The expression "silicone base" does not comprise compositions containing organic polymers having polycondensation-crosslinkable silica-containing groups.

The silicone bases according to the invention are described in detail in particular in numerous patents and they are commercially available.

These silicone bases may be single-component bases, i.e. bases that are packaged in a single package, and stable during storage in the absence of moisture, which can be cured in the presence of moisture, in particular moisture provided by the ambient air or by water generated within the base during the use thereof.

Apart from single-component bases, use may be made of two-component bases, i.e. bases that are packaged in two packages, which cure as soon as the poly-condensation catalyst according to the invention is incorporated. They are packaged, after incorporation of the catalyst, in two separate fractions, one of the fractions possibly containing, for example, only the catalyst according to the invention or a mixture with the crosslinking agent.

The silicone base B used to prepare the composition according to the invention comprises:
- at least one polyorganosiloxane oil C capable of crosslinking by polycondensation to give an elastomer;
- optionally, at least one crosslinking agent D;
- optionally, at least one adhesion promoter E; and
- optionally, at least one siliceous, organic and/or nonsiliceous mineral filler F.

The polyorganosiloxane oil C is preferably an α,ω-dihydroxypolydiorganosiloxane polymer which has a viscosity of between 50 and 5 000 000 mPa·s at 25° C., and the crosslinking agent D is preferably an organo-silicon compound bearing more than two hydrolyzable groups bonded to the silicon atoms per molecule. The polyorganosiloxane oil C may also be functionalized at its ends with hydrolyzable radicals obtained by condensation of a precursor bearing hydroxyl functions with a crosslinking silane bearing hydrolyzable radicals.

As crosslinking agent D, mention may be made of:
silanes of the following general formula:

$R^1_k Si(OR^2)_{(4-k)}$ in which the symbols $R^2$, which may be identical or different, represent alkyl radicals having from 1 to 8 carbon atoms, such as methyl, ethyl, propyl, butyl, pentyl or 2-ethylhexyl radicals, or $C_3$-$C_6$ oxyalkylene radicals, the symbol $R^1$ represents a linear or branched, saturated or unsaturated, aliphatic hydrocarbon-based group or a saturated or unsaturated and/or aromatic, monocyclic or polycyclic carbocyclic group, and k is equal to 0, 1 or 2; and
the partial hydrolysis products of this silane.

As examples of $C_3$-$C_6$ alkoxyalkylene radicals, mention may be made of the following radicals:
CH$_3$OCH$_2$CH$_2$—
CH$_3$OCH$_2$CH(CH$_3$)—
CH$_3$OCH(CH$_3$) CH$_2$—
C$_2$H$_5$OCH$_2$CH$_2$CH$_2$—

The symbol $R^1$ represents a $C_1$-$C_{10}$ hydrocarbon-based radical that encompasses:
- $C_1$-$C_{10}$ alkyl radicals such as methyl, ethyl, propyl, butyl, pentyl, 2-ethylhexyl, octyl or decyl radicals,
- vinyl and allyl radicals, and
- $C_5$-$C_8$ cycloalkyl radicals such as phenyl, tolyl and xylyl radicals.

The crosslinking agents D are products that are available on the silicones market; furthermore, their use in room-temperature curing compositions is known; it occurs in particular in French patents FR-A-1 126 411, FR-A-1 179 969, FR-A-1 189 216, FR-A-1 198 749, FR-A-1 248 826, FR-A-1 314 649, FR-A-1 423 477, FR-A-1 432 799 and FR-A-2 067 636.

Among the crosslinking agents D, preference is more particularly given to alkyltrialkoxysilanes, alkyl silicates and alkyl polysilicates, in which the organic radicals are alkyl radicals having from 1 to 4 carbon atoms.

As other examples of crosslinking agents D that may be used, mention is more particularly made of the following silanes:
propyltrimethoxysilane,
methyltrimethoxysilane,
ethyltrimethoxysilane,
vinyltriethoxysilane,
methyltriethoxysilane,
propyltriethoxysilane,
tetraethoxysilane,
tetrapropoxysilane,
1,2-bis(trimethoxysilyl)ethane,
1,2-bis(triethoxysilyl)ethane, and
tetraisopropoxysilane,
or else: CH$_3$Si(OCH$_3$)$_3$; C$_2$H$_5$Si(OC$_2$H$_5$)$_3$; C$_2$H$_5$Si(OCH$_3$)$_3$ CH$_2$=CHSi(OCH$_3$)$_3$; CH$_2$=CHSi(OCH$_2$CH$_2$OCH$_3$)$_3$; C$_6$H$_5$Si(OCH$_3$)$_3$; [CH$_3$][OCH(CH$_3$) CH$_2$OCH$_3$]Si[OCH$_3$]$_2$; Si(OCH$_3$)$_4$; Si(OC$_2$H$_5$)$_4$; Si(OCH$_2$CH$_2$CH$_3$)$_4$; Si(OCH$_2$CH$_2$CH$_2$CH$_3$)$_4$; Si(OC$_2$H$_4$OCH$_3$)$_4$; CH$_3$Si(OC$_2$H$_4$OCH$_3$)$_3$; ClCH$_2$Si(OC$_2$H$_5$)$_3$.

As other examples of crosslinking agent D, mention may be made of ethyl polysilicate or n-propyl polysilicate.

Use is generally made of 0.1 to 60 parts by weight of crosslinking agent D per 100 parts by weight of poly-organosiloxane C capable of crosslinking by polycondensation to give an elastomer.

Thus, the composition according to the invention may comprise at least one adhesion promoter E such as, for example, the organosilicon compounds bearing both:
(1) one or more hydrolyzable groups bonded to the silicon atom, and
(2) one or more organic groups substituted with radicals comprising a nitrogen atom or chosen from the group of (meth)acrylate, epoxy and alkenyl radicals, and even more preferably from the group constituted of the following compounds taken alone or as a mixture:
vinyltrimethoxysilane (VTMO);
3-glycidoxypropyltrimethoxysilane (GLYMO),
methacryloxypropyltrimethoxysilane (MEMO),
[H$_2$N(CH$_2$)$_3$]Si(OCH$_2$CH$_2$CH$_3$)$_3$;
[H$_2$N(CH$_2$)$_3$]Si(OCH$_3$)$_3$;
[H$_2$N(CH$_2$)$_3$]Si(OC$_2$H$_5$)$_3$;
[H$_2$N(CH$_2$)$_4$]Si(OCH$_3$)$_3$;
[H$_2$NCH$_2$CH(CH$_3$)CH$_2$CH$_2$]SiCH$_3$(OCH$_3$)$_2$;
[H$_2$NCH$_2$]Si(OCH$_3$)$_3$;
[n-C$_4$H$_9$—HN—CH$_2$]Si(OCH$_3$)$_3$;
[H$_2$N(CH$_2$)$_2$NH(CH$_2$)$_3$]Si(OCH$_3$)$_3$;
[H$_2$N(CH$_2$)$_2$NH(CH$_2$)$_3$]Si(OCH2CH$_2$OCH$_3$)$_3$;
[CH$_3$NH(CH$_2$)$_2$NH(CH$_2$)$_3$]Si(OCH$_3$)$_3$
[H(NHCH$_2$CH$_2$)$_2$NH(CH$_2$)$_3$]Si(OCH$_3$)$_3$

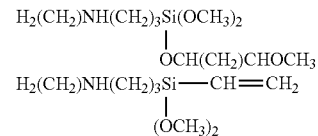

or polyorganosiloxane oligomers containing such organic groups at a content of greater than 20%.

For the single-component and two-component bases, use is made, as mineral fillers F, of very finely divided products, the average particle diameter of which is less than 0.1 µm. Among these fillers are fumed silicas and precipitated silicas; their BET specific surface area is generally greater than 40 m$^2$/g. These fillers may also be in the form of more coarsely divided products, having an average particle size of greater than 0.1 µm. As examples of such fillers, mention may be made of ground quartz, diatomaceous silicas, calcium carbonate, calcined clay, rutile-type titanium oxide, iron, zinc, chromium, zirconium or magnesium oxides, the various forms of alumina (hydrated or unhydrated), boron nitride, lithopone, barium metaborate, barium sulfate and glass microbeads; their specific surface area is generally less than 30 m²/g.

These fillers may have been surface-modified by treatment with the various organosilicon compounds customarily used for this purpose. Thus, these organo-silicon compounds may be organochlorosilanes, diorgano-cyclopolysiloxanes, hexaorganodisiloxanes, hexaorgano-disilazanes or diorgano-cyclopolysilazanes (French patents FR-A-1 126 884, FR-A-1 136 885 and FR-A-1 236 505, and British patent GB-A-1 024 234). The treated fillers contain, in most cases, from 3% to 30% of their weight of organosilicon compounds. The fillers may be constituted of a mixture of several types of fillers of different particle size; thus, for example, they may be constituted of from 30% to 70% of finely divided silicas with a BET specific surface area of greater than 40 m²/g and of from 70% to 30% of more coarsely divided silicas with a specific surface area of less than 30 m²/g.

The purpose of introducing fillers is to confer good mechanical and rheological characteristics on the elastomers that result from the curing of the compositions in accordance with the invention.

In combination with these fillers, use may be made of inorganic and/or organic pigments and also agents that improve the thermal resistance (salts and oxides of rare-earth elements such as ceric oxides and hydroxides) and/or the fire resistance of the elastomers. For example, it is possible to use the cocktails of oxides described in international application WO 98/29488. Among the agents for improving fire resistance, mention may be made of halogenated organic derivatives, organic phosphorus derivatives, platinum derivatives, such as chloroplatinic acid (its reaction products with alkanols or ethers), or platinous chloride-olefin complexes. These pigments and agents together represent at most 20% of the weight of the fillers.

Other customary auxiliary agents and additives may be incorporated into the composition according to the invention; these are chosen according to the applications in which said compositions are used.

The silicone base used to prepare the composition according to the invention may comprise:
  100 parts of polyorganosiloxane oil C capable of crosslinking by polycondensation to give an elastomer;
  0 to 20 parts of a crosslinking agent D;
  0 to 20 parts of an adhesion promoter E; and
  0 to 50 parts of filler F.

In addition to the main constituents, nonreactive linear polyorganosiloxane polymers G may be introduced with the intention of acting on the physical characteristics of the compositions in accordance with the invention and/or the mechanical properties of the elastomers resulting from the curing of these compositions.

These nonreactive linear polyorganosiloxane polymers G are well known; they comprise more especially: $\alpha,\omega$-bis(triorganosiloxy)diorganopolysiloxane polymers with viscosities of at least 10 mPa·s at 25° C., formed essentially from diorganosiloxy units and from at most 1% of monoorganosiloxy and/or siloxy units, the organic radicals bonded to the silicon atoms being chosen from methyl, vinyl and phenyl radicals, at least 60% of these organic radicals being methyl radicals and at most 10% being vinyl radicals. The viscosity of these polymers can reach several tens of millions of mPa·s at 25° C.; they therefore include oils with a fluid to viscous appearance and soft to hard gums. They are prepared according to the usual techniques described more specifically in French patents FR-A-978 058, FR-A-1 025 150, FR-A-1 108 764 and FR-A-1 370 884. Use is preferably made of $\alpha,\omega$-bis(trimethylsiloxy)dimethyl-polysiloxane oils with a viscosity ranging from 10 mPa·s to 1000 mPa·s at 25° C. These polymers, which act as plasticizers, can be introduced in a proportion of at most 70 parts, preferably from 5 to 20 parts, per 100 parts of polyorganosiloxane oil C capable of crosslinking by polycondensation.

The compositions according to the invention can also advantageously comprise at least one silicone resin H. These silicone resins are branched organopolysiloxane polymers which are well known and which are commercially available. They have, per molecule, at least two different units chosen from those of formula $R'''_3SiO_{1/2}$ (M unit), $R'''_2SiO_{2/2}$ (D unit), $R'''SiO_{3/2}$ (T unit) and $SiO_{4/2}$ (Q unit). The R''' radicals are identical or different and are chosen from linear or branched alkyl radicals or vinyl, phenyl or 3,3,3-tri-fluoropropyl radicals. Preferably, the alkyl radicals have from 1 to 6 carbon atoms inclusive. More particularly, mention may be made, as alkyl R radicals, of methyl, ethyl, isopropyl, tert-butyl and n-hexyl radicals. These resins are preferably hydroxylated and have, in this case, a weight content of hydroxyl groups of between 5 and 500 meq/100 g.

As examples of resins, mention may be made of MQ resins, MDQ resins, TD resins and MDT resins.

In order to produce the compositions in accordance with the invention, it is necessary, in the case of the single-component compositions, to use equipment which makes it possible to intimately mix the various fundamental constituents in a moisture-free environment, with or without a supply of heat, optionally added to which constituents are the above-mentioned adjuvants and additives. All these ingredients can be loaded into the equipment in any order of introduction. Thus, it is possible to first of all mix the organopolysiloxane oils C and the fillers F and then to add to the paste obtained the crosslinking agents D, the compounds E and the catalyst according to the invention. It is also possible to mix the oils C, the crosslinking agents D, the compounds E and the fillers F and to subsequently add the catalyst according to the invention. During these operations, the mixtures can be heated to a temperature within the range of 50-180° C. under atmospheric pressure or under a reduced pressure in order to promote the removal of volatile materials.

The single-component compositions in accordance with the invention, used as such, i.e. undiluted, or in the form of dispersions in diluents, are stable during storage in the absence of water and cure at low temperatures (after removal of solvents in the case of dispersions) in the presence of water so as to form elastomers.

After the deposition of the compositions as they are, onto solid substrates, in a humid atmosphere, it is observed that a process of curing to give elastomers occurs; it takes place from the outside to the inside of the mass deposited. A skin forms first at the surface, then the crosslinking occurs in depth. The complete formation of the skin, which results in a tack-free feel of the surface, requires a period of time of a few minutes; this period of time depends on the degree of relative humidity of the atmosphere surrounding the compositions and on the crosslink-ability of said compositions.

Moreover, the in-depth curing of the deposited layers, which must be sufficient to allow the demolding and the handling of the elastomers formed, requires a longer period of time. Specifically, this period of time depends not only on the factors mentioned above for the formation of the tack-free feel, but also on the thickness of the deposited layers, said thickness generally lying between 0.5 mm and several centimeters. The single-component compositions can be used for multiple applications such as jointing in the construction industry, assembling the most diverse materials (metals, plastics, natural and synthetic rubbers, wood, board, earthenware, brick, ceramic, glass, stone, concrete, masonry units), insulating electrical conductors, the potting of electronic circuits, or the preparation of molds used for manufacturing articles made of synthetic resins or foams.

The production of the two-component compositions in accordance with the invention is also carried out by mixing the various constituents in suitable equipment. In order to obtain homogeneous compositions, it is preferable to first of all mix the polymers A with the fillers C; the whole mixture can be heated for at least 30 minutes at a temperature above 80° C., so as to complete the wetting of the fillers by the oils. The other constituents, i.e. the crosslinking agents, the catalyst and, optionally, various additives and adjuvants and even water, can be added to the mixture obtained, preferably brought to a temperature below 80° C., for example of around room temperature.

The compositions in accordance with the invention can be used for multiple applications, such as jointing and/or bonding in the construction industry or the transportation industry (examples: automobile, aerospace, railroad, maritime and aeronautical industries), assembling the most diverse materials (metals, plastics, natural and synthetic rubbers, wood, boards, polycarbonate, earthenware, brick, ceramic, glass, stone, concrete and masonry units), insulating electrical conductors, the potting of electronic circuits, and the preparation of molds used for manufacturing articles made of synthetic resins or foams.

Thus, another subject of the invention consists of a two-component system which is a precursor of the organopolysiloxane composition according to the invention and as defined above and which can be vulcanized to give a silicone elastomer via poly-condensation reactions and which is characterized in that it is in two separate parts P1 and P2 intended to be mixed so as to form said composition, and in that one of these parts comprises the catalyst according to the invention and as defined above as catalyst of the reaction for polycondensation of organopolysiloxanes and the crosslinking agent D, whereas the other part is free of the abovementioned species and comprises:
  for 100 parts by weight of the polyorganosiloxane oil(s) C capable of crosslinking by polycondensation to give an elastomer, and
  from 0.001 to 10 part(s) by weight of water.

Another subject of the invention also consists of a single-component polyorganosiloxane composition which is stable during storage in the absence of moisture and which crosslinks, in the presence of water, to give an elastomer, characterized in that it comprises:
  at least one crosslinkable linear polyorganosiloxane that has functionalized ends of alkoxy, oxime, acyl and/or enoxy type, preferably alkoxy type,
  a filler, and
  the catalyst of the polycondensation reaction according to the invention and as defined above.

Single-component bases are described in detail, for example, in patents EP 141 685, EP 147 323, EP 102 268, EP 21 859, FR 2 121 289 and FR 2 121 631, cited by way of reference.

It is possible to add, to these single-component bases, adhesion promoters E chosen, for example, from organosilicon compounds simultaneously bearing, on the one hand, organic groups substituted with radicals chosen from the group of amino, ureido, isocyanate, epoxy, alkenyl, isocyanurate, hydantoyl, guanidino and mercaptoester radicals and, on the other hand, hydrolyzable groups, in general alkoxy groups bonded to the silicon atoms. Examples of such adhesion agents are described in U.S. Pat. Nos. 3,517,001, 4,115,356, 4,180,642, 4,273,698 and 4,356,116 and in European patents EP 31 996 and EP 74 001.

Two-component bases are described in detail, for example, in patents EP 118 325, EP 117 772, EP 10 478, EP 50 358, EP 184 966, U.S. Pat. No. 3,801,572 and U.S. Pat. No. 3,888,815, cited by way of reference.

Other advantages and features of the present invention will become apparent on reading the following examples given by way of illustration and that are in no way limiting.

EXAMPLES

I) Preparation of the Catalysts According to the Invention a) 1-Butyl-2,3-diisopropylguanidine (A1)

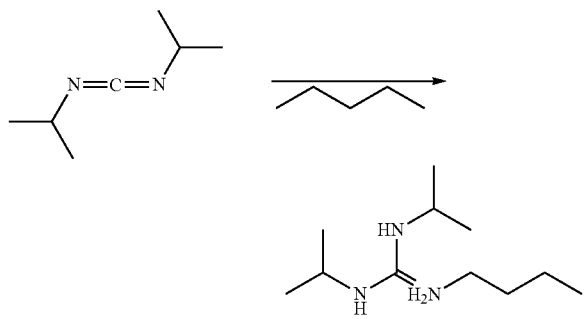

A mixture of 33 g of N-butylamine (0.45 mol) and 19 g of diisopropylcarbodiimide (0.15 mol) is refluxed for 3 h 30. GC analysis then shows a conversion of greater than 99.5% of the diisopropylcarbodiimide. The colorless final mixture is concentrated at 60° C. under 20 mbar for 2 h so as to give 29 g of a colorless and virtually odorless liquid of low viscosity, corresponding to the expected guanidine (yield 96.7%).

$^1$H NMR/CDCl$_3$ (ppm): 0.93 (3H, t), 1.14 (12H, d), 1.37 (2H, sex), 1.52 (2H, quint), 3.01 (2H, t), 3.57 (2H, m).

b) 1-Butyl-2,3-diisopropyl-1-methylguanidine (A3)

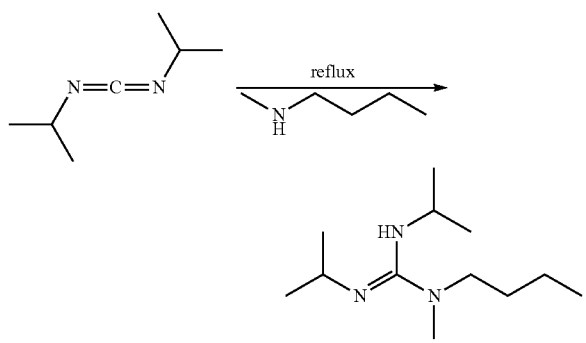

A mixture of 32.68 g of N-butyl-N-methylamine (0.375 mol) and 23.66 g of diisopropylcarbodiimide (0.1875 mol) is refluxed for 3 h. GC analysis then shows a conversion of greater than 99.5% of the diisopropylcarbodiimide. The colorless final mixture is concentrated at 60° C. under 5 mbar for 2 h so as to give 40 g of a colorless and virtually odorless liquid of low viscosity, corresponding to the expected guanidine (yield 100%).

¹H NMR/CDCl₃ (ppm): 0.88 (3H, t), 1.06 (12H, d), 1.26 (2H, sex), 1.46 (2H, quint), 2.67 (3H, s), 3.05 (2H, t), 3.35 (2H, m).

c) 1-Butyl-2,3-dicyclohexylguanidine (A2)
RN—CAS=60006-40-8

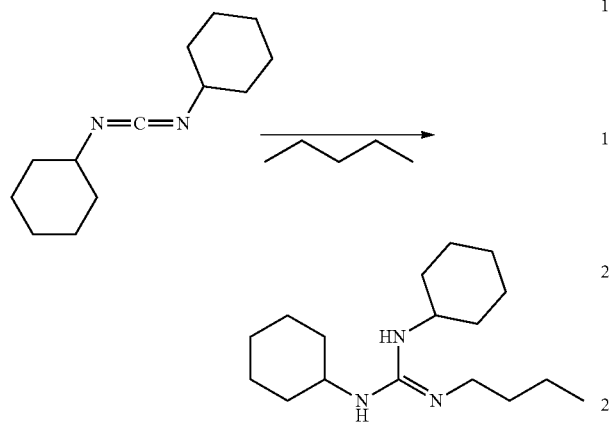

A mixture of 15.69 g of N-butylamine (0.214 mol) and 22.13 g of dicyclohexylcarbodiimide (0.107 mol) is refluxed for 2 h. GC analysis then shows a conversion of greater than 99.6% of the dicyclohexylcarbodiimide. The colorless final mixture is concentrated at 60° C. under 1 mbar for 2 h so as to give 29.7 g of a colorless and virtually odorless liquid of medium viscosity, corresponding to the expected guanidine (yield 99%).

d) 1-Butyl-2,3-dicyclohexyl-1-methylguanidine (A4)

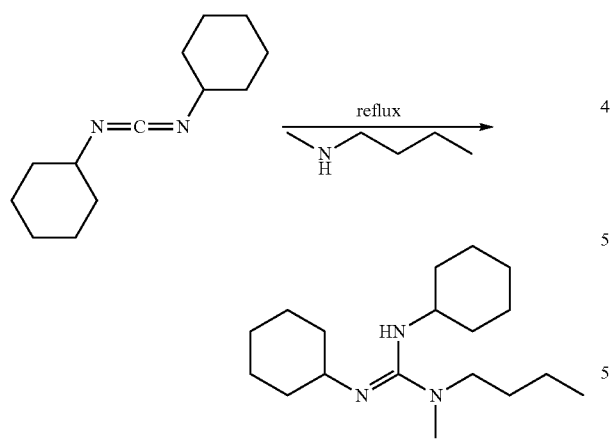

A mixture of 17.78 g of N-butyl-N-methylamine (0.204 mol) and 21.05 g of dicyclohexylcarbodiimide (0.102 mol) is refluxed for 3 h. GC analysis then shows a conversion of greater than 99.5% of the dicyclohexyl-carbodiimide. The colorless final mixture is concentrated at 60° C. under 1 mbar for 2 h so as to give 29.9 g of a colorless and virtually odorless liquid of medium viscosity, corresponding to the expected guanidine (yield 99.7%).

¹H NMR/CDCl₃ (ppm): 0.89 (3H, t), 1-1.4 (10H, m), 1.47 (2H, quint), 1.5-2 (12H, several m), 2.67 (3H, s), 2.90 (1H, m), 2.97 (1H, m), 3.06 (2H, t).

e) 1,2-Dicyclohexyl-3-piperidylguanidine (A5)
RN—CAS 60006-25-9

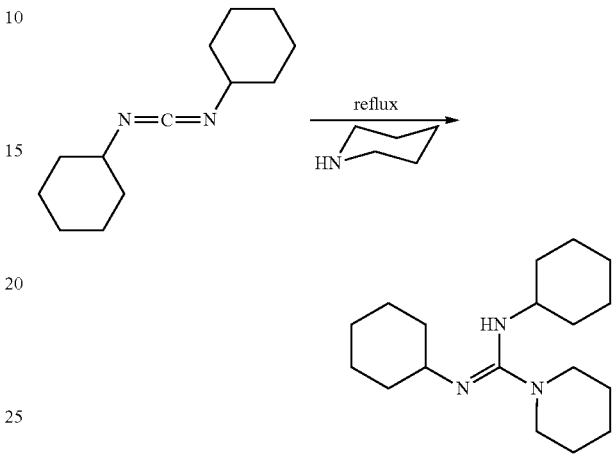

A mixture of 11.69 g of piperidine (0.137 mol) and 14.16 g of dicyclohexylcarbodiimide (0.0686 mol) is refluxed for 3 h 30. GC analysis then shows a conversion of greater than 99.7% of the dicyclohexyl-carbodiimide. The colorless final mixture is concentrated at 60° C. under 1 mbar for 2 h so as to give 19.9 g of a colorless and virtually odorless, very viscous liquid, corresponding to the expected guanidine (yield 99.5%).

f) 1,2-Dicyclohexyl-3-pyrrolidylguanidine (A6)
RN—CAS 60006-28-2

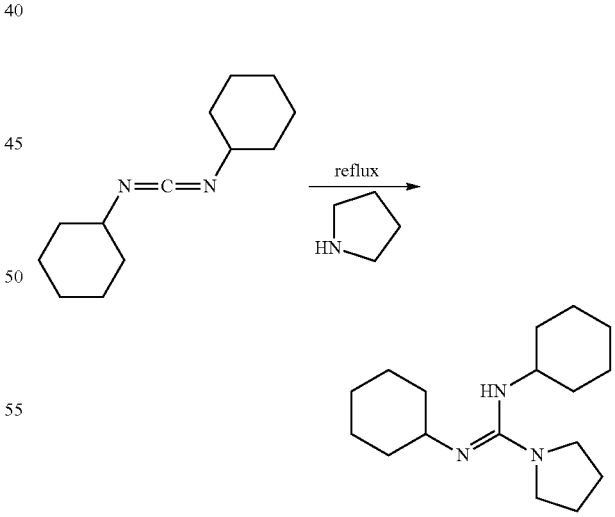

A mixture of 19.2 g of pyrrolidine (0.27 mol) and 18.6 g of dicyclohexylcarbodiimide (0.09 mol) is refluxed for 4 h. GC analysis then shows a conversion of greater than 99.8% of the dicyclohexylcarbodiimide. The colorless final mixture is concentrated at 60° C. under 1 mbar for 1 h so as to give 24.9 g of a colorless and virtually odorless liquid of medium viscosity, corresponding to the expected guanidine (yield 99.6%).

II. Preparation of Single-Component Compositions a) Paste Test—Vinyltrimethoxysilane Crosslinker

The paste used was prepared as follows: added, with stirring, to a mixture of 3464 g of an α,ω-dihydroxylated oil with a viscosity of 20 000 centipoises containing 0.066% of OH and of 120 g of vinyltrimethoxysilane were 16 g of a 2% by weight solution of lithium hydroxide in methanol, then, after 5 min, 400 g of AE55 fumed silica were added. The mixture was devolatilized under vacuum and then stored in a moisture-free environment.

For each test, the catalyst tested was mixed with 50 g of this paste, and then the catalytic potential was evaluated in 3 ways:
- the skin-over time (SOT), time at the end of which surface crosslinking is observed, on a 2 mm film;
- the persistence of a tacky feel at 48 h,
- the hardness (Shore A hardness) of a 6 mm thick bead under controlled conditions (23° C. and 50% relative humidity) and over increasing times (2, 3, 4, 7 and 14 days), and also after 7 days (7D) at room temperature (RT) followed by 7 days at 100° C. In the results tables, the symbol ">" corresponds to the hardness values measured on the upper part of the bead and the symbol "<" corresponds to the hardness values measured on the lower part of the bead that is less exposed to the ambient air than the upper part.

Various catalysts according to the invention were tested. By way of comparison, as above, the following were also tested:
- a tin-based catalyst: dibutyltin dilaurate (DBTDL), and
- 1,1,3,3-tetramethylguanidine (TMG) which is described in international application WO 2004/020525. The results are given in table I below:

TABLE I

| Reference | Structure | mol/Sn | % by weight | SOT stick min | Tacky feel at 48 h | Shore A hardness over 6 mm | | | | | |
|---|---|---|---|---|---|---|---|---|---|---|---|
| | | | | | | 2D >< | 3D >< | 4D >< | 7D >< | 14D >< | 7D RT + 7D 100° C. >< |
| Comparative (DBTDL) | | 1 | 0.88 | 10 | no | 34 26 | 35 30 | 35 30 | 35 29 | 35 30 | 35 28 |
| Comparative (TMG) | 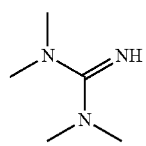 | 4 | 0.64 | 2 | yes | 2 1 | 2 1 | / | 4 3 | 2 1 | 1 1 |
| Invention (A1) | 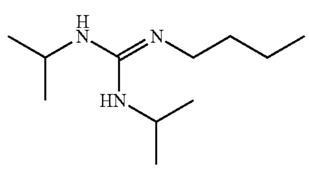 | 3 | 0.84 | 1 | no | 36 26 | 36 28 | 37 28 | 38 28 | 38 30 | 34 27 |
| | | 1.5 | 0.42 | 2 | no | 35 22 | 36 26 | 36 27 | 37 28 | 39 28 | 36 26 |
| | | 0.75 | 0.21 | 2 | yes | 30 4 | 32 6 | 33 9 | 35 14 | 37 21 | 35 21 |
| Invention (A2) | 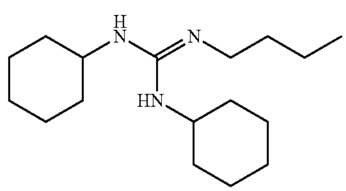 [SMILES: CCCCN=C(NC1CCCCC1)NC1CCCCC1] | 1.5 | 0.59 | 1 | no | 34 27 | 35 28 | 35 30 | 36 30 | 37 31 | 31 25 |
| Invention (A3) | 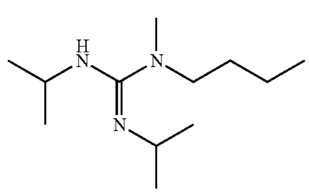 | 3 | 0.9 | 3 | no | 35 27 | 36 29 | 36 29 | 35 29 | 37 31 | 37 30 |
| | | 1.5 | 0.46 | 5 | no | 35 21 | 37 28 | 37 30 | 37 30 | 39 31 | 37 31 |
| | | 0.75 | 0.23 | 6 | yes | 31 12 | 33 21 | 35 24 | 36 27 | 39 30 | 37 27 |
| | | 0.375 | 0.11 | 12 | yes | 22 4 | 26 6 | 28 10 | 28 13 | 32 23 | 31 21 |
| Invention (A4) | 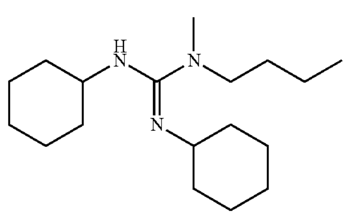 [SMILES: CCCCN(C)/C(=N\C1CCCCC1)NC1CCCCC1] | 0.75 | 0.31 | 5 | no | 35 24 | 36 28 | 37 29 | 37 29 | 37 30 | 37 30 |
| | | 0.375 | 0.15 | 7 | no | 30 13 | 32 19 | 33 23 | 34 26 | 35 28 | 35 29 |

1,1,3,3-Tetramethylguanidine (TMG) does not enable crosslinking of the silicone oil, even though it is at molar concentrations much higher than the guanidines according to the invention (A1) to (A4). The 1,2,3-tri-substituted guanidines (A1) and (A2) result in very short skin-over times and in elastomers. The 1,2,3,3-tetrasubstituted guanidines (A3) and (A4) make it possible not only, by adapting the contents to very low values, to modulate the lengths of the skin-over times, but also to obtain elastomers which are very thermally stable and slightly higher degrees of crosslinking than with the tin catalyst (DBTDL). These results show that the catalysts according to the invention (A1) to (A4), which are nontoxic, result in a more efficient catalysis than the tin-based catalysts (DBTDL) and than tetramethylguanidine (TMG). The catalysts according to the invention can therefore advantageously replace the existing catalysts.

b) Paste Test—Vinyltriethoxysilane Crosslinker

The paste used was prepared as follows: added, with stirring, to a mixture of 857.5 g of an α,ω-dihydroxylated oil with a viscosity of 20 000 centipoises containing 0.066% of OH, and of 38.5 g of vinyltriethoxysilane were 4 g of a 4% by weight solution of lithium hydroxide in methanol, and then, after 20 min, 100 g of AE55 fumed silica were added. The mixture was devolatilized under vacuum and then stored in a moisture-free environment. For each test, the catalyst tested was mixed with 50 g of this paste, and then the catalytic potential was evaluated in the same way as before.

Various catalysts according to the invention were tested.

By way of comparison, as above, the following was also tested:

a tin-based catalyst: dibutyltin dilaurate (DBTDL).

The results are given in table II below:

The tin catalyst gives a good hardness but only at 14 days with this much less reactive system. Moreover, the skin-over time is prohibitive. With the catalysts according to the invention, the skin-over times are short and can be modulated according to the content, and the hardness kinetics are much faster: equivalent levels of hardness are obtained. An elastomer that releases virtually only ethanol is therefore made possible with the catalysts according to the invention.

III) Preparation of Two-Component Compositions

The comparison of the activity of the catalysts according to the invention with respect to the standard catalyst (dimethyltin bisneodecanoate—UL28, comparative 1) and to 1,1,3,3-tetramethylguanidine (comparative 2), was carried out on a simplified system: mixed with 25 g of an α,ω-dihydroxylated oil with a viscosity of 14 000 centipoises containing 0.065% of OH are 1.06 g of "advanced" (=partially hydrolyzed) ethyl silicate, and then the same molar amount (0.7 mmol) of catalyst. The pot-life or gel time, followed by the hardness of a 6 mm thick slug were measured under controlled conditions (23° C. and 50% relative humidity) and over increasing times. In the following table, the symbol ">" corresponds to the hardness values measured on the upper part of the slug and the symbol "<" corresponds to the hardness values measured on the lower part of the slug that is less exposed to the ambient air than the upper part.

The results are given in table III below:

TABLE II

| Reference | Product | nb eq 1 eq = 0.70 nM | % by weight | SOT stick min | tacky feel at 48 h | Shore A hardness over 6 mm 2D >< | 3D >< | 4D >< | 7D >< | 14D >< | 7D RT + 7D 100° C. >< |
|---|---|---|---|---|---|---|---|---|---|---|---|
| Comparative | DBTDL | 1 | 0.9 | 60 | no | 10 7 | 16 12 | 20 16 | 26 22 | 32 29 | 33 29 |
| Invention A1 | [structure] | 3 1.5 | 0.8 0.5 | 4 5 | no no | 28 16 18 7 | 31 22 21 12 | 32 24 23 14 | 33 26 26 17 | 33 27 30 22 | 32 25 28 20 |
| Invention A3 | [structure] | 3 1.5 | 0.9 0.5 | 12 20 | no yes | 29 17 18 9 | 31 24 23 16 | 31 26 26 21 | 32 28 31 25 | 33 28 33 30 | 34 30 32 27 |
| Invention A4 | [structure] | 3 1.5 | 1.2 0.6 | 8 10 | no no | 31 24 29 18 | 32 27 31 24 | 32 27 32 27 | 33 28 33 27 | 33 28 33 29 | 33 29 34 29 |

TABLE III

| Catalyst | Pot-life | Shore hardness A 24 h > | Shore hardness A 24 h < | Shore hardness A 48 h > | Shore hardness A 48 h < | Shore hardness A 6 days > | Shore hardness A 6 days < | Shore hardness A (n days) > | Shore hardness A (n days) < | (n d) |
|---|---|---|---|---|---|---|---|---|---|---|
| Comparative 1 (Sn) | 6 min | 22.5 | 22.5 | not measured | not measured | not measured | not measured | 23 | 23 | (20 d) |
| Comparative 2 (TMG) | 7 min | no cross-linking | no cross-linking | no cross-linking | no cross-linking | no cross-linking | no cross-linking | no cross-linking | no cross-linking | |
| Invention (A1) | 30 s | 23 | 9 | not measured | not measured | 24 | 25 | 22 | 18 | (28 d) |
| Invention (A3) | 2 min 30 s | 23 | 9 | 24 | 22 | not measured | not measured | 22 | 21 | (13 d) |
| Invention (A4) | 8-9 min | 21 | 19 | 21 | 21 | 24 | 24 | 23 | 23 | (13 d) |

The tetrasubstituted guanidine (A4) is particularly efficient with a pot-life and hardness kinetics which are entirely comparable to the tin catalyst reference.

IV) RTV-2: Silicone Composition that can be Crosslinked at Room Temperature Via a Polycondensation Reaction The two-component compositions described in detail in table IV are prepared. The ingredients listed below are the constituents used for examples 1 to 4 and comparatives 1 and 2:

a1: hydroxylated polydimethylsiloxane oil blocked at each of the chain ends with a $(CH_3)_2(OH)SiO_{0.5}$ unit with a viscosity of 14 000 mPa·s at 25° C., a2: hydroxylated polydimethylsiloxane oil blocked at each of the chain ends with a $(CH_3)_2(OH)SiO_{0.5}$ unit with a viscosity of 750 mPa·s at 25° C., a3: hydroxylated polydimethylsiloxane oil blocked at each of the chain ends with a $(CH_3)_2(OH)SiO_{0.5}$ unit with a viscosity of 50 mPa·s at 25° C., b1: fumed silica having a BET specific surface area of 200 $m^2/g$, treated with HMDZ, dispersed in a mixture of a1 and of a polydimethylsiloxane oil blocked at each of the chain ends with a $(CH_3)_3SiO_{0.5}$ unit, b2: ground quartz having an average particle diameter of 10 μm, c: water, d1: catalyst according to the invention (A4), d2: catalyst according to the invention (A2), d3: catalyst according to the invention (A3), d4: comparative 1,1,3,3-tetramethylguanidine (TMG), d5: comparative Fomrez® catalyst UL-28: dimethylbis[(1-oxoneodecyl)oxy]stannane=$[C_9H_{19}COO]_2Sn(Me)_2$, e: ethyl polysilicate.

TABLE IV

RTV2 compositions (parts by weight)

| Ingredients | Example 1 invention | Example 2 invention | Example 3 invention | Example 4 invention | Comparative example 1 (TMG) | Comparative example 2 (Sn) |
|---|---|---|---|---|---|---|
| a1 | 20 | 20 | 20 | 20 | 20 | 20 |
| a2 | 1 | 1 | 0 | | 1 | 1 |
| a3 | 1 | 1 | 1 | 0.2 | 1 | 0 |
| b1 | 60.20 | 60.20 | 60.20 | 60.20 | 60.20 | 60.20 |
| b2 | 18 | 18 | 18 | 18 | 18 | 18 |
| c | 0 | 0 | 0 | 0.1 | 0 | 0.1 |
| d1 | 0.26 (1 eq) | | 0.26 (1 eq) | | | |
| d2 | | 0.25 (1 eq) | | | | |
| d3 | | | | 0.19 (1 eq) | | |
| d4 | | | | | 0.1 (1 eq) | |
| d5 | | | | | | 0.44 (1 eq) |
| e | 1.5 | 1.5 | 3 | 1.5 | 1.5 | 1.5 |

2) Evaluation of the Compositions

The results of table V demonstrate the efficiency of the catalytic systems claimed. In addition, example 1 demonstrates the advantage of using the guanidine 1 for obtaining elastomers which do not contain toxic products and which have a pot-life suitable for the application (i.e. a pot-life that is long enough to allow it to be used, but short enough to obtain an article that can be handled at the latest after 24 h at 23° C.)

TABLE V

Crosslinking kinetics (pot-life and Shore A hardness acquisition kinetics)

| | Example 1 invention | Example 2 invention | Example 3 invention | Example 4 invention | Comparative example 1 (TMG) |
|---|---|---|---|---|---|
| Pot-life (min.) | 8 min | 2 min | 3 min | 3 min | 7 min |
| SAH after 24 h at 23° C. (top/bottom) | 21/19 | 20/20 | 17/18 | 12/13 | non demoldable |
| SAH after 2 d at 23° C. (bottom) | 22 | 22 | 26 | 20 | non demoldable |
| Appearance of the crosslinked slug | Homogeneous | Homogeneous | Homogeneous | Homogeneous | non demoldable |

Shore A hardness, denoted SAH: measurements carried out according to the instructions of the ASTM-D2240 standard on the upper and lower part of the slug.

The results in table VI show that the elastomer obtained has good mechanical properties, similar to those obtained with a tin-based catalyst.

TABLE VI

Mechanical properties

| Mechanical properties | SAH 4 d (bottom) | Tear strength (N/mm) | TS (Mpa) | EB (%) |
|---|---|---|---|---|
| Example 1 - invention | 22 | 18 | 3.2 | 455 |
| Comparative example 2 - (Sn) | 22 | 20 | 3.5 | 400 |

Tear strength (N/mm, measurements carried out according to the instructions of the ASTM-D624A standard).
TS = tensile strength (MPa, measurements carried out according to the instructions of the ASTM-D412 or AFNOR-T-46002 standard).
EB = elongation at break (%, measurements carried out according to the instructions of the ASTM-D412 or AFNOR-T-46002 standard).

TABLE VII

Shore A hardness after heat treatment at 220° C.

| (Time in h) | Example 1 invention | Comparative example 2 (Sn) |
|---|---|---|
| 0 | 26 | 23 |
| 4 | | |
| 7 | | 18 |
| 14 | | 23 |
| 21 | 25 | 25 |
| 22 | | |
| 28 | 24 | |
| 45 | | 28 |
| 54 | | |
| 69 | 23 | 28 |
| 86 | | |
| 120 | 23 | |

Table VII above (see also FIG. 1) also demonstrates the very good heat resistance of the elastomers crosslinked in the presence of the catalytic system claimed: specifically, the Shore A hardness of these elastomers remains constant after a heat treatment at 220° C., unlike the elastomers catalyzed with tin complexes (at 220° C.: loss of Shore A hardness, followed by large increase in Shore A hardness).

All of these results show that the catalytic system according to the invention results in elastomers being obtained that have properties equivalent to or superior to the control, in particular as regards the heat resistance properties (no change in Shore A hardness after a long-duration heat treatment at 220° C.), accompanied by very rapid kinetics that are compatible with industrial production rates.

The invention claimed is:

1. An organopolysiloxane composition which does not contain any metal catalyst, said composition comprising, firstly, a silicone base B comprising at least one polyorganosiloxane oil which can be crosslinked via a polycondensation reaction so as to form a silicone elastomer and, secondly, a catalytically effective amount of at least one polycondensation catalyst A which is a nonsilylated organic compound selected from the group consisting of the following compounds (A1) to (A6):

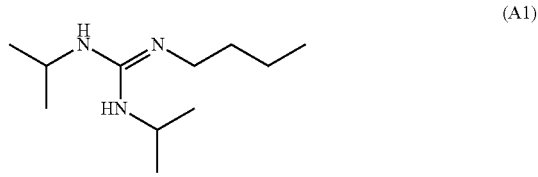

(A1)

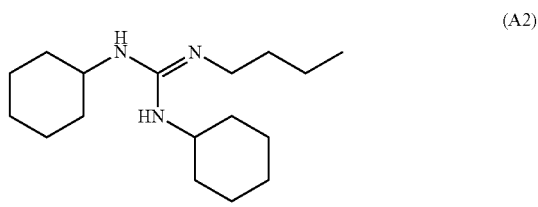

(A2)

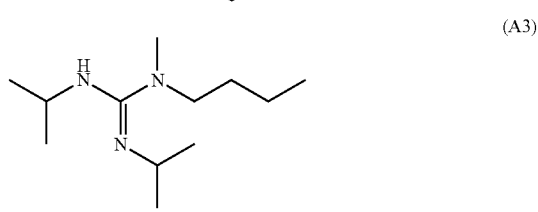

(A3)

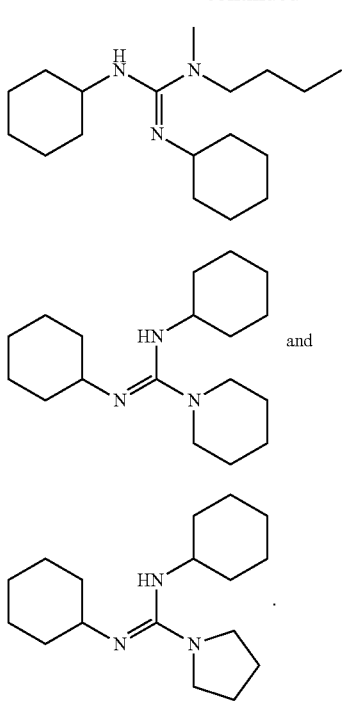

2. The composition as claimed in claim 1, wherein the silicone base B comprises:
   at least one polyorganosiloxane oil C capable of crosslinking by polycondensation to give an elastomer;
   optionally, at least one crosslinking agent D;
   optionally, at least one adhesion promoter E; and
   optionally, at least one siliceous, organic and/or nonsiliceous mineral filler F.

3. The organopolysiloxane composition as claimed in claim 2, wherein the silicone base B comprises:
   for 100 parts by weight of at least one polyorganosiloxane oil C capable of crosslinking by polycondensation, which is an α,ω-dihydroxydiorganopolysiloxane reactive polymer of which the organic radicals are hydrocarbon-based radicals, and are optionally selected from the group consisting of: alkyls containing from 1 to 20 carbon atoms; cycloalkyls containing from 3 to 8 carbon atoms; alkenyls containing from 2 to 8 carbon atoms and cycloalkenyls containing from 5 to 8 carbon atoms,
   from 0.1 to 60 parts by weight of at least one crosslinking agent D selected from the group consisting of: polyalkoxysilanes, products originating from the partial hydrolysis of a polyalkoxysilane, and polyalkoxysiloxanes,
   from 0 to 60 parts by weight of an adhesion promoter E,
   from 0 to 250 parts by weight of at least one siliceous, organic and/or nonsiliceous mineral filler F,
   from 0.001 to 10 parts by weight of water,
   from 0 to 100 parts by weight of at least one nonreactive, linear polyorganosiloxane polymer G comprising of a linear homopolymer or copolymer of which, per molecule, the monovalent organic substituents, which may be identical to or different from one another, and which are bonded to the silicon atoms, are selected from alkyl, cycloalkyl, alkenyl, aryl, alkylarylene and arylalkylene radicals,
   from 0 to 20 parts by weight of a coloring base or of a coloring agent H,
   from 0 to 70 parts by weight of at least one polyorganosiloxane resin I, and
   from 0 to 20 parts of at least one auxiliary additive J, optionally selected from the group consisting of plasticizers, crosslinking retardants, mineral oils, antimicrobial agents or heat stabilizers, such as titanium, iron or cerium oxides, and
   wherein the organopolysiloxane composition comprises from 0.1 to 50 parts by weight of said at least one polycondensation catalyst.

4. An elastomer obtained or obtainable by crosslinking and curing a composition of claim 1.

5. An elastomer obtained or obtainable by crosslinking and curing a composition of claim 2.

6. The organopolysiloxane composition as claimed in claim 3, wherein the silicone base B comprises from 5 to 200 parts by weight, of at least one siliceous, organic and/or nonsiliceous mineral filler F.

7. The organopolysiloxane composition as claimed in claim 1, wherein the polycondensation catalyst is between 0.1% and 10% by weight of a total mass of the organopolysiloxane composition.

8. The organopolysiloxane composition as claimed in claim 1, wherein the organopolysiloxane composition does not contain alkyltin-based catalysts.

9. The organopolysiloxane composition as claimed in claim 2, wherein the silicone base B comprises:
   100 parts of the at least one polyorganosiloxane oil C;
   0 to 20 parts of the at least one crosslinking agent D;
   0 to 20 parts of the at least one adhesion promoter E; and
   0 to 50 parts of the at least one siliceous, organic and/or non-siliceous mineral filler F.

10. A two-component system which is a precursor of an organopolysiloxane composition comprising:
    at least one polyorganosiloxane oil C capable of crosslinking by polycondensation to give an elastomer;
    optionally, at least one crosslinking agent D;
    optionally, at least one adhesion promoter E; and
    optionally, at least one siliceous, organic and/or nonsiliceous mineral filler F;
    and which is vulcanizable to give a silicone elastomer via a polycondensation reaction and wherein said system is in two separate parts P1 and P2 intended to be mixed so as to form said composition, and further wherein one of said parts comprises a polycondensation catalyst A as catalyst of a reaction for polycondensation of a organopolysiloxane and the crosslinking agent D, and the other part is free thereof, and wherein the other part comprises:
    for 100 parts by weight of the polyorganosiloxane oil(s) C capable of crosslinking by polycondensation to give an elastomer, and
    from 0.001 to 10 part(s) by weight of water;
    wherein the polycondensation catalyst A is a nonsilylated organic compound
    selected from the group consisting of the following compounds (A1) to (A6):

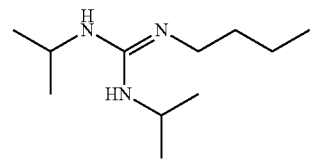

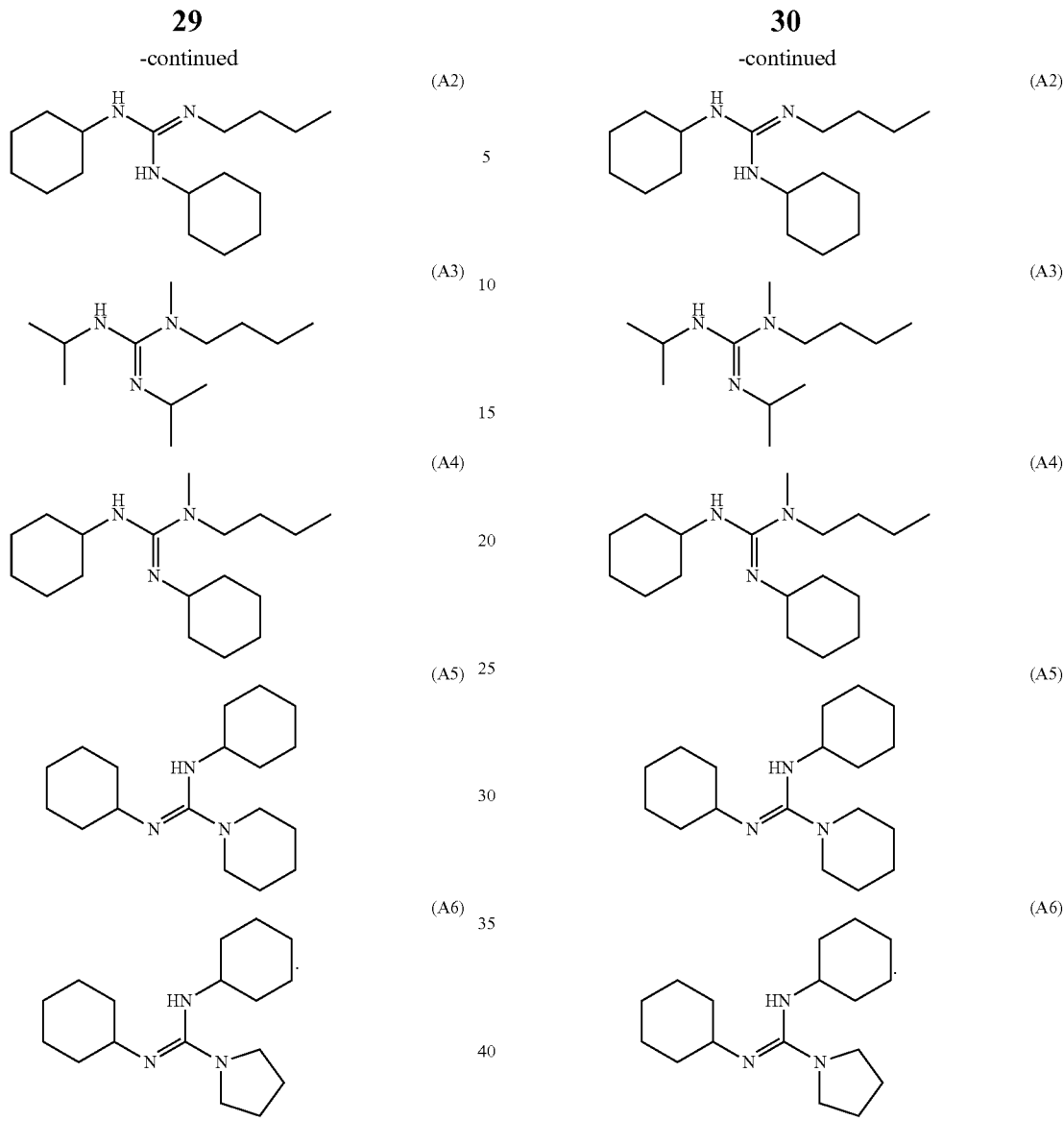

11. An elastomer obtained by crosslinking and curing of the two-component system as defined in claim 10.

12. A single-component polyorganosiloxane composition which is stable during storage in the absence of moisture and which crosslinks, in the presence of water, to give an elastomer, said composition comprising:
- at least one crosslinkable linear polyorganosiloxane oil C which has functionalized ends of alkoxy, oxime, acyl and/or enoxy type,
- at least one crosslinking agent D,
- at least one filler F, and
- at least one catalyst of the polycondensation reaction which is a polycondensation catalyst A which is a non-silylated organic compound
selected from the group consisting of the following compounds (A1) to (A6):

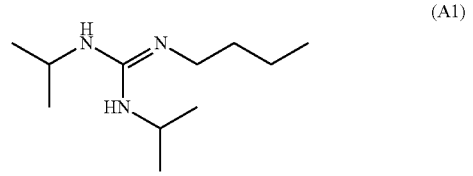

13. The single-component polyorganosiloxane composition as claimed in claim 12, wherein the crosslinkable linear polyorganosiloxane oil C which has functionalized ends of alkoxy type is prepared in situ by reaction, in the presence of a catalytically effective amount of lithium hydroxide, of a linear diorganopolysiloxane comprising a hydroxyl group bonded to a silicon atom at each chain end, with at least one polyalkoxysilane of formula (II) below:

$$(R^4)_c(R^5)_a Si(OR^6)_{4-(a+c)} \tag{II}$$

in which:
- a is equal to 0, 1 or 2,
- c is equal to 0, 1 or 2,
- the sum of a+c is equal to 0, 1 or 2,
- $R^4$ represents an aliphatic, cyclanic or aromatic, substituted or unsubstituted, and saturated or unsaturated $C_1$ to $C_{13}$ hydrocarbon-based monovalent radical, it being possible for $R^4$ to be identical to $R^5$,
- $R^5$ represents an aliphatic, cyclanic or aromatic, substituted or unsubstituted, and saturated or unsaturated $C_1$ to $C_{13}$ hydrocarbon-based monovalent radical which can comprise an epoxy, primary, secondary or tertiary amine, or mercapto function, and $R^6$ represents an aliphatic organic radical containing from 1 to 8 carbon atoms, optionally selected from alkyl radicals, alkyl ether radicals, alkyl ester radicals, alkyl ketone radicals, alkylcyano radicals and aralkyl radicals containing from 7 to 13 carbon atoms, it being understood that alkoxy groups of the silane of formula (II) can each have a different meaning for $R^6$ or the same meaning.

14. The single-component polyorganosiloxane composition as claimed in claim 13 wherein the crosslinking agent D or the polyalkoxysilane of formula (II) are selected from the group consisting of:
vinyltriethoxysilane,
methyltriethoxysilane,
propyltriethoxysilane,
tetraethoxysilane,
1,2-bis(triethoxysilyl)ethane,
$C_2H_5Si(OC_2H_5)_3$, and
$Si(OC_2H_5)_4$.

15. An elastomer obtained or obtainable by crosslinking and curing a composition of claim 12.

16. A compound of formula:

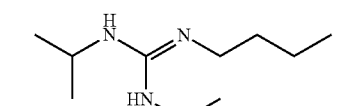
(A1)

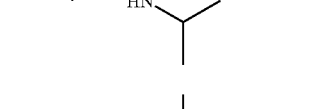
(A3)

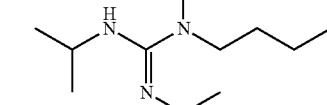
(A4)

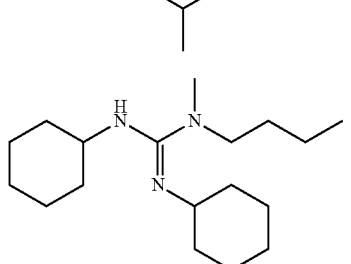

17. A catalyst for an organopolysiloxane polycondensation reaction, comprising a polycondensation catalyst A which is a nonsilylated organic compound selected from the group consisting of the following compounds (A1) to (A6):

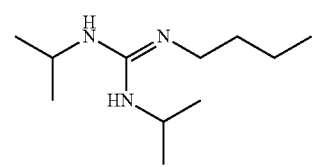
(A1)

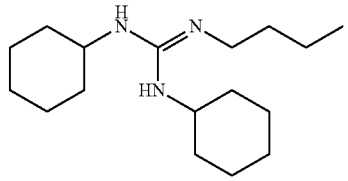
(A2)

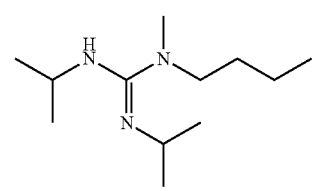
(A3)

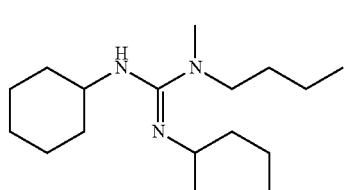
(A4)

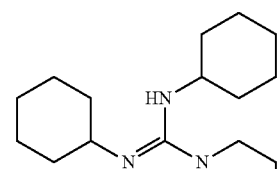
(A5)

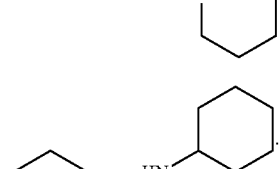
(A6)

* * * * *